(12) United States Patent
Jacobsen (10) Patent No.: US 11,844,597 B2
(45) Date of Patent: *Dec. 19, 2023

(54) WIRELESS PRESSURE MEASUREMENT AND MONITORING FOR SHUNTS

(71) Applicant: Medtronic Navigation, Inc., Louisville, CO (US)

(72) Inventor: Brad Jacobsen, Erie, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/845,398

(22) Filed: Jun. 21, 2022

(65) Prior Publication Data

US 2022/0313101 A1 Oct. 6, 2022

Related U.S. Application Data

(63) Continuation of application No. 16/298,183, filed on Mar. 11, 2019, now Pat. No. 11,375,915, which is a
(Continued)

(51) Int. Cl.
*A61B 5/03* (2006.01)
*A61B 5/00* (2006.01)
(Continued)

(52) U.S. Cl.
CPC ............. *A61B 5/031* (2013.01); *A61B 5/002* (2013.01); *A61B 5/061* (2013.01); *A61B 5/6847* (2013.01);
(Continued)

(58) Field of Classification Search
CPC ......... A61B 5/031; A61B 5/002; A61B 5/061; A61B 5/6847; A61B 5/6852;
(Continued)

(56) References Cited

U.S. PATENT DOCUMENTS 2,718,144 A 9/1955 Hornfeck
3,017,885 A 1/1962 Robicsek
(Continued)

FOREIGN PATENT DOCUMENTS

CN 201968740 U 9/2011
EP 683890 A1 11/1995
(Continued)

OTHER PUBLICATIONS

Korean Office Action, Request for the Submission of an Opinion, corresponding to Korean Patent Application No. 10-2017-7031236, dated Feb. 6, 2023.
(Continued)

*Primary Examiner* — Sanjay Cattungal
(74) *Attorney, Agent, or Firm* — Harness, Dickey & Pierce, P.L.C.

(57) ABSTRACT

Disclosed is a system that includes pressure sensors to assist in monitoring pressure at a selected location. Pressure sensors may be applied to or incorporated into catheters and/or shunts positioned within a patient. A monitoring system may then receive signals from the pressure sensors to monitor pressure at the location over time.

19 Claims, 5 Drawing Sheets

Related U.S. Application Data continuation of application No. 14/673,972, filed on Mar. 31, 2015, now Pat. No. 10,226,193.

(51) Int. Cl.

| | | |
|---|---|---|
| *A61M 27/00* | (2006.01) | |
| *A61B 34/20* | (2016.01) | |
| *A61B 6/12* | (2006.01) | |
| *A61B 6/00* | (2006.01) | |
| *A61B 5/06* | (2006.01) | |
| *A61M 25/00* | (2006.01) | |
| *A61B 90/00* | (2016.01) | |

(52) U.S. Cl.
CPC ............ *A61B 5/6852* (2013.01); *A61B 5/746* (2013.01); *A61B 5/7425* (2013.01); *A61B 6/12* (2013.01); *A61B 6/4441* (2013.01); *A61B 6/487* (2013.01); *A61B 6/504* (2013.01); *A61B 34/20* (2016.02); *A61M 27/006* (2013.01); *A61B 5/0031* (2013.01); *A61B 5/062* (2013.01); *A61B 5/066* (2013.01); *A61B 2034/2051* (2016.02); *A61B 2090/363* (2016.02); *A61B 2090/376* (2016.02); *A61B 2560/0214* (2013.01); *A61B 2560/063* (2013.01); *A61B 2562/0247* (2013.01); *A61B 2562/04* (2013.01); *A61M 2025/0002* (2013.01)

(58) Field of Classification Search
CPC ......... A61B 5/7425; A61B 5/746; A61B 6/12; A61B 6/4441; A61B 6/487; A61B 6/504; A61B 34/20; A61B 5/0031; A61B 5/062; A61B 5/066; A61B 2034/2051; A61B 2090/363; A61B 2090/376; A61B 2560/0214; A61B 2560/063; A61B 2562/0247; A61B 2562/04; A61B 2560/0219; A61B 5/0002; A61B 5/032; A61M 27/006; A61M 2025/0002; A61M 2202/0464; A61M 2210/0693
See application file for complete search history.

(56) References Cited

U.S. PATENT DOCUMENTS

| | | | |
|---|---|---|---|
| 3,409,763 A | 11/1968 | Schoppe, Jr. | |
| 3,669,116 A | 6/1972 | Heyer | |
| 3,847,020 A | 11/1974 | Jurschak | |
| 3,960,143 A | 6/1976 | Terada | |
| 4,377,169 A | 3/1983 | Banks | |
| 4,382,445 A | 5/1983 | Sommers | |
| 4,385,636 A | 5/1983 | Cosman | |
| 4,581,943 A | 4/1986 | Feller | |
| 4,588,085 A | 5/1986 | Sussman | |
| 4,593,703 A | 6/1986 | Cosman | |
| 4,605,395 A | 8/1986 | Rose et al. | |
| 4,741,730 A | 5/1988 | Dormandy, Jr. et al. | |
| 4,931,039 A | 6/1990 | Coe et al. | |
| 5,000,731 A | 3/1991 | Wong et al. | |
| 5,038,773 A | 8/1991 | Norlien et al. | |
| 5,069,674 A | 12/1991 | Fearnot et al. | |
| 5,207,684 A | 5/1993 | Nobles | |
| 5,304,114 A | 4/1994 | Cosman et al. | |
| 5,535,633 A | 7/1996 | Kofoed et al. | |
| 5,728,061 A | 3/1998 | Ahmed | |
| 5,772,625 A | 6/1998 | Krueger et al. | |
| 5,865,801 A * | 2/1999 | Houser .................. | A61B 5/036 607/101 |
| 5,928,182 A | 7/1999 | Kraus et al. | |
| 5,980,480 A | 11/1999 | Rubenstein et al. | |
| 6,053,873 A | 4/2000 | Govari et al. | |
| 6,085,599 A | 7/2000 | Feller | |
| 6,264,625 B1 | 7/2001 | Rubenstein et al. | |
| 6,432,050 B1 | 8/2002 | Porat et al. | |
| 6,585,677 B2 | 7/2003 | Cowan, Jr. et al. | |
| 6,689,085 B1 | 2/2004 | Rubenstein et al. | |
| 6,840,917 B2 | 1/2005 | Marion | |
| 6,875,192 B1 | 4/2005 | Saul et al. | |
| 6,905,474 B2 | 6/2005 | Borgesen | |
| 6,926,691 B2 | 8/2005 | Miethke | |
| 7,025,742 B2 | 4/2006 | Rubenstein et al. | |
| 7,037,288 B2 | 5/2006 | Rosenberg et al. | |
| 7,041,083 B2 | 5/2006 | Chu et al. | |
| 7,118,548 B2 | 10/2006 | Borgesen | |
| 7,290,454 B2 | 11/2007 | Liu | |
| 7,337,678 B2 | 3/2008 | Thakre et al. | |
| 8,088,091 B2 | 1/2012 | Thomas et al. | |
| 8,644,907 B2 | 2/2014 | Hartmann et al. | |
| 10,226,193 B2 | 3/2019 | Jacobsen | |
| 2002/0123714 A1 | 9/2002 | Saul et al. | |
| 2003/0032915 A1 | 2/2003 | Saul | |
| 2003/0045870 A1 | 3/2003 | Madsen | |
| 2003/0135147 A1 | 7/2003 | Rosenberg et al. | |
| 2003/0159697 A1 | 8/2003 | Wallace | |
| 2003/0216666 A1 | 11/2003 | Ericson et al. | |
| 2004/0030279 A1 | 2/2004 | Rubenstein et al. | |
| 2004/0068201 A1 | 4/2004 | Saul | |
| 2004/0092908 A1 | 5/2004 | Harper et al. | |
| 2004/0092909 A1 | 5/2004 | Harper et al. | |
| 2004/0102761 A1 | 5/2004 | Ahmed | |
| 2004/0122348 A1 | 6/2004 | Hokanson et al. | |
| 2004/0147871 A1 | 7/2004 | Burnett | |
| 2004/0167385 A1 * | 8/2004 | Rioux .................... | A61B 5/026 600/373 |
| 2004/0215067 A1 | 10/2004 | Stiger et al. | |
| 2004/0236309 A1 | 11/2004 | Yang | |
| 2004/0243192 A1 | 12/2004 | Hepp et al. | |
| 2004/0260229 A1 | 12/2004 | Meir | |
| 2004/0267187 A1 | 12/2004 | Rosenberg | |
| 2005/0055009 A1 | 3/2005 | Rosenberg | |
| 2005/0085764 A1 | 4/2005 | Borgesen | |
| 2005/0085841 A1 | 4/2005 | Eversull et al. | |
| 2005/0096582 A1 | 5/2005 | Burnett | |
| 2005/0113802 A1 | 5/2005 | Watson | |
| 2005/0267413 A1 | 12/2005 | Wang et al. | |
| 2006/0151923 A1 | 7/2006 | Wilkowske et al. | |
| 2006/0211946 A1 | 9/2006 | Mauge et al. | |
| 2006/0228453 A1 | 10/2006 | Cromack et al. | |
| 2007/0038171 A1 | 2/2007 | Mayer | |
| 2007/0083193 A1 * | 4/2007 | Werneth ............... | A61B 5/7445 606/41 |
| 2007/0131279 A1 | 6/2007 | Thakre et al. | |
| 2007/0225687 A1 | 9/2007 | House | |
| 2007/0261496 A1 | 11/2007 | Jonsson et al. | |
| 2008/0065008 A1 | 3/2008 | Barbut et al. | |
| 2008/0208245 A1 | 8/2008 | Hoffman | |
| 2008/0214983 A1 | 9/2008 | Mauge et al. | |
| 2009/0093806 A1 * | 4/2009 | Govari ............... | A61B 18/1492 606/34 |
| 2009/0262980 A1 | 10/2009 | Markowitz et al. | |
| 2009/0281566 A1 * | 11/2009 | Edwards ................ | A61B 5/062 606/214 |
| 2009/0297574 A1 * | 12/2009 | Ahn ....................... | A61B 5/412 604/27 |
| 2010/0030312 A1 * | 2/2010 | Shen .................... | A61B 34/20 607/122 |
| 2011/0237937 A1 | 9/2011 | Kalpin et al. | |
| 2011/0270081 A1 | 11/2011 | Burg et al. | |
| 2012/0041295 A1 | 2/2012 | Schultz | |
| 2013/0303971 A1 | 11/2013 | Budgett et al. | |
| 2014/0012130 A1 | 1/2014 | Jacobsen et al. | |
| 2014/0024703 A1 | 1/2014 | Shimizu et al. | |
| 2014/0243703 A1 * | 8/2014 | Schmidt ................ | A61B 5/031 600/561 |
| 2014/0276367 A1 * | 9/2014 | Kersten ................ | A61M 27/00 604/22 |
| 2014/0276660 A1 | 9/2014 | Eckermann | |
| 2014/0323852 A1 | 10/2014 | Wald et al. | |
| 2016/0228678 A1 * | 8/2016 | Cargill .................... | C12Q 1/54 |
| 2017/0354337 A1 | 12/2017 | Schmidt et al. | |

(56) References Cited

U.S. PATENT DOCUMENTS

FOREIGN PATENT DOCUMENTS

| EP | 745213 | A1 | 12/1996 |
|---|---|---|---|
| EP | 0888795 | A1 | 1/1999 |
| EP | 0904728 | A2 | 3/1999 |
| EP | 0921836 | A1 | 6/1999 |
| EP | 1007113 | A1 | 6/2000 |
| EP | 1050264 | A1 | 11/2000 |
| EP | 1327459 | A1 | 7/2003 |
| EP | 1491137 | A2 | 12/2004 |
| EP | 1512428 | A1 | 3/2005 |
| EP | 1552784 | A1 | 7/2005 |
| GB | 1271361 | A | 4/1972 |
| JP | 200558775 | A | 3/2005 |
| JP | 2006511271 | A | 4/2006 |
| JP | 2006255422 | A | 9/2006 |
| JP | 2009106633 | A | 5/2009 |
| JP | 2010528818 | A | 8/2010 |
| WO | 8301387 | A1 | 4/1983 |
| WO | 8702255 | A1 | 4/1987 |
| WO | 9117779 | A1 | 11/1991 |
| WO | 9519549 | A1 | 7/1995 |
| WO | 9802202 | A1 | 1/1998 |
| WO | 9818510 | A1 | 5/1998 |
| WO | 9830275 | A1 | 7/1998 |
| WO | 9953990 | A1 | 10/1999 |
| WO | 0136014 | A2 | 5/2001 |
| WO | 2004073768 | A2 | 9/2004 |
| WO | 2006009467 | A2 | 1/2006 |
| WO | 2007015934 | A2 | 2/2007 |
| WO | 2007075349 | A2 | 7/2007 |
| WO | 2007127305 | A2 | 11/2007 |
| WO | 2007127619 | A1 | 11/2007 |
| WO | 2008005440 | A2 | 1/2008 |
| WO | 2008027322 | A1 | 3/2008 |

OTHER PUBLICATIONS

Canadian Office Action regarding Application No. 2,981,280, dated Jan. 29, 2023.
Kestle, John R.W., M.D. Shunt malfunction. J. Neurosurg 113 (2010) pp. 1270-1272.
Kestler, John R.W., M.D., Shunt insertion. J. Neurosurg. DOI: 10.3171/2012.4. JNS12485 (2013) 2 pages.
Mc10reshaping electronics. Electrophysiology. MC10. Retrieved from http://www.mc10inc.com/medical-devices/interventional-catheters/electrophysiology (Jan. 27, 2015). 5 pages.
Pressure and Temperature, Sensor, Ultra-Miniature, High-Temperature, Low Frequency (134 KHz) RFID Passive Wireless Sensor. Phase IV Engineering Inc. Retrieved from http://www.phaseivengr.com/product/pressure-temperature-ulta-miniature-low-frequency. (Aug. 2014) 4 pages.
Kim, D., Lu, N., Ghaffari, R., et al., Materials for multifunctional balloon catheters with capabilities in cardiac electrophysiological mapping and ablation therapy. Nature Materials. (Mar. 2011) DOI: 10.1038/NMAT2971. pp. 1-8.
Li, X., and Kan, E. A wireless low-range pressure sensor based on P(VDF-TrFFE) piezoelectric resonance. Sensors and Actuators A: Physical. DOI: 10.16/j.sna.2010.08.022 (2010) pp. 457-463.
International Search Report and Written Opinion dated Sep. 5, 2016 for PCT/US2016/023862 which claims benefit of U.S. Appl. No. 14/673,972, filed Mar. 31, 2015.
International Preliminary Report on Patentability dated Oct. 12, 2017 in corresponding International Application No. PCT/US2016/023862.
Australian Examination Report for Application No. 2016243358 dated Nov. 18, 2019.
Office Action regarding Japanese Patent Application No. 2017550673, dated Feb. 5, 2020.
Office Action dated Mar. 4, 2020 in corresponding Chinese Application No. 201680029920.3.
Office Action dated Oct. 16, 2020 in corresponding Chinese Application No. 201680029920.3.
Office Action dated Nov. 2, 2020, in corresponding Japanese Application No. 2017-550673.
Third Office Action in corresponding Chinese Application No. 201680029920.3 dated Jan. 25, 2021.
Office Action regarding Chinese Patent Application No. 201680029920.3, dated Nov. 3, 2021.
European Office Action regarding European Application No. 16712708.3, dated Oct. 22, 2021.
First Australian Examination Report regarding Australian Application No. 2020250199, dated Feb. 18, 2022.
Japanese Office Action regarding Application No. 2021-032241, dated Mar. 2, 2022.
Canadian Office Action regarding Patent Application No. 2981280, dated Mar. 7, 2022.

* cited by examiner

WIRELESS PRESSURE MEASUREMENT AND MONITORING FOR SHUNTS

CROSS-REFERENCE TO RELATED APPLICATIONS

The application is a continuation of U.S. patent application Ser. No. 16/298,183 filed on Mar. 11, 2019, which is a continuation of U.S. patent application Ser. No. 14/673,972 filed on Mar. 31, 2015, now issued U.S. Pat. No. 10,226,193 issued Mar. 12, 2019. The entire disclosure of the above applications are incorporated herein by reference.

FIELD

The subject disclosure relates to monitors for various systems, including, in various embodiments, pressure sensors for catheters, drains, and shunts to be positioned in a subject.

BACKGROUND

This section provides background information related to the present disclosure which is not necessarily prior art.

A shunt may be inserted into a system for various purposes. Generally, a shunt allows transfer of a fluid, such as a liquid fluid, from a first location to a second location. A shunt may be used to bypass a pre-existing pathway or to create a new pathway in case OF damage to a pre-existing pathway or non-existence of a pathway.

In various procedures, a shunt may be inserted into the anatomy of a subject, such as a human subject, to allow drainage of fluid, such as cerebral spinal fluid. Without drainage of cerebral spinal fluid, pressure may build in an enclosed area, such as within the cerebral ventricles, and cause damage to the brain of a subject. A shunt, therefore, may be provided to ensure an appropriate pressure be maintained within the cerebral ventricles of a subject.

SUMMARY

This section provides a general summary of the disclosure, and is not a comprehensive disclosure of its full scope or all of its features.

In some occasions, various processes may partially or fully occlude shunts placed in a subject. Such a malfunctioning or failed shunt will allow pressure to build and cause damage, such as to a brain of a subject. This damage may occur before signs or symptoms clinically present again in a subject. This damage may be temporary, long term, or permanent. To minimize this damage, real time pressure monitoring of cerebral spinal fluid in cerebral ventricles may be useful.

Disclosed is a system that includes pressure sensors to assist in monitoring pressure at a selected location. Pressure sensors may be applied to or incorporated into catheters and/or shunts positioned within a patient. The shunt and/or a catheter may be permanently implanted in a patient. According to various embodiments, a catheter and a shunt, alone or together, within a patient may provide immediate relief of pressure within a patient. A shunt may also be appropriately placed within any selected system, such as any fluid system including that within an automobile engine, aircraft engine, or the like. Also, other non-human or non-moving subjects may have fluid pathways, such as cooling or lubricating fluid pathways, that may be blocked from time to time where a shunt may be provided to assist in ensuring appropriate drainage from one location to another of a fluid.

A pressure sensor may be provided with the shunt or catheter to assist in measuring the pressure at or near the location to be drained. The pressure sensor may be provided as a substantially small sensor that can be integrated onto a surface of a catheter, such as a plurality of traces formed on the surface or near a surface of a catheter, or as an independent sensor that can be integrated into the shunt or catheter. For example, the pressure sensor may be formed on a thin film and applied to the shunt or catheter. Further, the sensor may connect to circuitry to allow wired or wireless to transfer information transfer to selected systems, such as a surgical navigation system including a StealthStation® surgical navigation system and/or a monitoring system such as a CareLink® monitoring system both sold by Medtronic, Inc., having a place of business in Minnesota, USA. Alternative systems, such as any wireless receiver system, including a portable computer system, may be used to receive incremental or bulk transfers of data including a pressure signal that includes values of pressure measurements. Further, the wireless systems may be either battery powered (i.e. including an on-board power system) or may be passive (e.g. including a radiative or inductive power system). Inductive or radiative power systems can include those disclosed in U.S. patent application Ser. No. 13/045,686, filed Mar. 11, 2011, incorporated herein by reference.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1A:
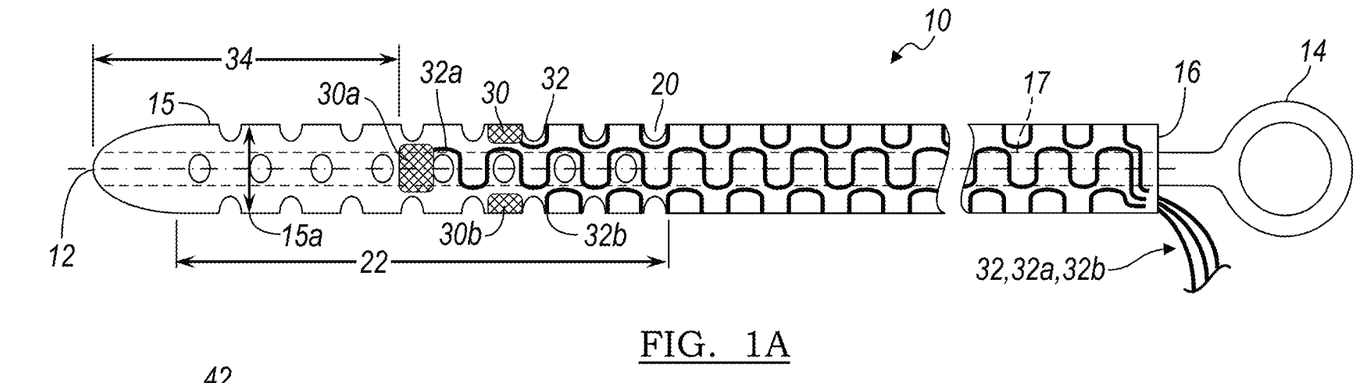
FIG. 1A is a schematic illustration of a shunt including one or more sensors.
Figure 1B:
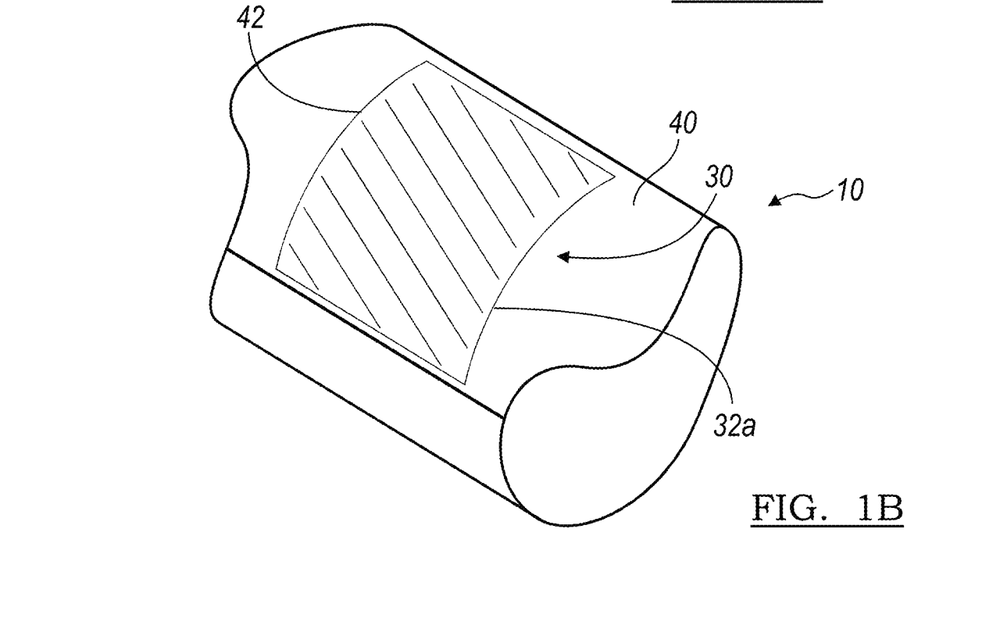
FIG. 1B is a detailed view of a sensor formed on a surface of the shunt of FIG. 1A.

With reference to FIGS. 1A and 1B, a catheter 10 is illustrated. It is understood that a shunt may have a similar structure and may include various sensors, as discussed herein. Also, a catheter or a shunt may be generally referred to as an elongated instrument that may be hollow or includes a lumen 17. It is understood, unless explicitly stated otherwise, that reference to a catheter, shunt, elongated hollow instrument is not meant to disregard similar structures unless specifically so stated.

The catheter 10 can extend from a distal terminal end 12 along a length to a proximal terminal end 16 that can be positioned in an appropriate system or portion of anatomy. Exemplary shunt systems include those sold by Medtronic, Inc. including the LP Shunt sold by Medtronic Neurosurgery, having a place of business in Goleta, California, and may further include various valves and flow controlled system, including Strata® valves, Delta® valves and other valve and flow controlled systems also sold by Medtronic, Inc. and/or Medtronic Neurosurgery. Further, the catheter 10 may be included as or provided as a catheter, including the Ares™ antibiotic catheter also sold by Medtronic Neurosurgery.

The catheter 10 may be inserted or positioned within the patient using various techniques such as with a stylet or elongated member 14 inserted into the catheter 10 via the proximal terminal end 16. It is understood that reference to any specific tracked instrument is not intended to limit the discussion to a single or specific trackable instrument, but may relate to any disclosed herein, unless specifically stated otherwise. The proximal terminal end 16 may include an opening and may be an access to the lumen 17 extending partially or completely the length of the catheter 10 towards the distal end 12. The catheter 10, however, may be closed and sealed at the distal terminal end 12. The stylet 14, as discussed further herein, may also be used to assist in navigating using various surgical navigation techniques, as also discussed further herein. The stylet 14, however, may provide selected rigidity to the catheter 10 during insertion of catheter 10 into the selected patient, or appropriate subject, including a non-living or non-human subject. As discussed above, the catheter 10 may be a catheter such as that generally known in the art, including the Ares™ catheter sold by Medtronic Neurological. Accordingly, various fixation mechanisms and clips may be provided that are movable or fixed relative to the catheter 10, but are generally known in the art.

The catheter 10 includes an exterior wall 15 that has a maximum cross-sectional dimension 15a through which a wall portal or hole 20 may be formed. The holes 20 allow for ingress or egress of a fluid into the lumen 17 of the catheter 10. The hole 20 may include a plurality of holes 20 that extend along a selected length, such as a length 22 of the catheter 10. The length 22 may extend to the distal terminal end 12 or may be positioned proximal to the distal terminal end 12.

Regardless, the holes 20 allow for a material to enter into the catheter 10 or exit the catheter 10. According to various embodiments, including use of the catheter 10 with a cerebral spinal fluid shunt system, cerebral spinal fluid (CSF) may enter into a catheter 10 to be passed through the lumen 17 to a selected collection position. As is generally understood in the art, the collection point or exit from the lumen 17 may be into a flow control valve and then into a collection system, including an external bag or container, or positioned internally into a patient such as near the abdominal cavity within the peritoneum membrane.

Generally, it is selected to maintain a predetermined or selected pressure or pressure range within a ventricle within a brain inside of a skull cavity of a patient, as illustrated further herein. The determination of the pressure within the ventricle may be measured with a pressure sensor 30 positioned or formed on the catheter 10 that is positioned within the ventricle. The portals 20 and the catheter 10 allow for the CSF to move into the catheter 10 from the ventricle. Accordingly, the pressure sensor 30 positioned amongst the portals 20 or within the region or length 22 of the catheter 10 allow for the measurement of pressure in the same region from which the CSF is to be removed, including the ventricle.

The pressure sensor 30 may be interconnected with a monitoring system via a wire or connector 32 that may run along a length of the catheter 10, such as to the proximal terminal end 16. A length of wire or other connector may then interconnect with a selected monitoring or transmission system, as discussed further herein. Also, more than one of the pressure sensors 30 may be provided such as pressure sensors 30a and 30b in addition to the pressure sensor 30. It is understood that each of the pressure sensors 30-30b may be connected with a selected wire or conductor 32, 32a, and 32b to a select data monitoring or transmission system. The connectors 32-32b may be applied directly to the catheter 10, including a surface thereof, or be provided on a printed circuit board integrated to the catheter 10. The connectors 32-32b may, however, be similar to those disclosed in U.S. Pat. App. Pub. No. 2014/0012130, incorporated herein by reference. Further, the pressure sensors 30-30b may be identical or nearly identical except for location, including size, sensitivity, etc. It is further understood, that only one sensor 30 may be provided and/or that a signal is selected to be received or transmitted from only the one sensor 30.

Figure 2:
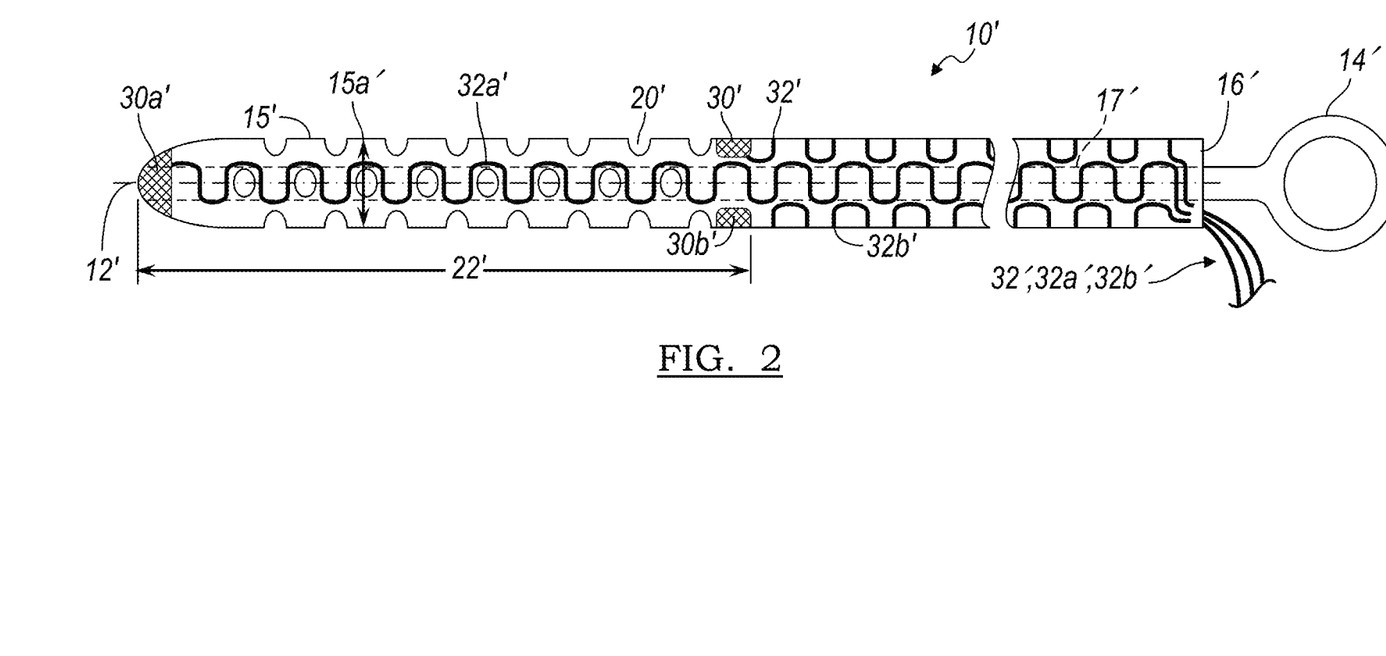
FIG. 2 is a schematic illustration of a shunt including pressure sensors, as illustrated in FIG. 1B and selected locations.

As illustrated in FIG. 1A, a most distal pressure sensor, including the pressure sensor 30a, is positioned a distance 34 from the distal terminal end 12. Further, the other pressure sensors 30 and 30b are positioned more proximal of the distal most pressure sensor 30a. It is understood, however, that the pressure sensors 30-30b may be positioned at any appropriate location along with the catheter 10, including being positioned only within the length 22 or at other appropriate locations, as discussed further herein. The pressure sensors 30 may be located to maximize information relevant for navigation or long term monitoring, or both. Pressure sensors 30-30b may be relevant to long term monitoring and may be placed as illustrated in FIG. 1A. Pressure sensors 30'-30b' may be relevant to navigation and may include those at the shunt distal tip and at the proximal end of the holes as illustrated in FIG. 2. It is understood, however, that all of the pressure sensors may be placed on a single device. As illustrated in FIG. 1B, the pressure sensor 30 may be formed on a surface 40 of the catheter 10. The surface 40 may be an external surface, such as on the external wall 15, and the pressure sensor 30 may be formed as a thin film 42 that may be placed on the surface according to various techniques. Further, the thin film 42 may include widths and lengths of about 0.2 millimeters (mm) to about 0.5 mm and a thickness of about 0.01 mm to about 0.1 mm. The thin films 42 may be connected to conductive traces, such as including widths of about 0.01 mm to about 0.04 mm that are laminated onto the surface 40 or may include vapor deposition techniques, or other appropriate forming techniques. Also, it is understood that the surface 40 may not be an external most surface, but may be overlaid with a selected material, such as polymer sheath or cover.

The pressure sensor 30-30b, therefore, is to be provided such that a maximum cross-sectional dimension of the catheter 15a, especially within the length 22, is increased by less than about 20% when the pressure sensor is included. Generally, it is selected to include the increase in dimension to be less than about 0.1 mm to about 0.3 mm, including about 0.2 mm. Thus, the inclusion of the pressure sensor 30-30*b* does not effectively increase the dimension of the catheter 10. Thus, the catheter 10 that includes the pressure sensor 30-30*b* may include substantially the same efficacy as previously used catheters, such as the Ares™ catheter.

Nevertheless, the pressure sensor 30 may be appropriately exposed to the environment external to or at the outer surface of the catheter 10 to be able to appropriately monitor pressure in an area, including the ventricle of a brain. Accordingly, the pressure sensor 30, or the plurality of pressure sensors 30, 30*a* and 30*b* may sense pressure at the location on the catheter 10 where they are placed and transmit the sensed pressure along the connectors 32-32*b* for appropriate monitoring of the pressure within the ventricle or other selected position of the catheter 10 including the pressure sensors 30-30*b*. As discussed herein, a wireless communication system may also be provided to transmit a signal from the pressure sensor 30-30*b*.

Generally, the pressure sensor 30-30*b* may measure a pressure at or near the holes 20 of the catheter 10. The measured pressure may be pressure value that is transmitted as a pressure signal, wirelessly or wired. Pressure values may be determined in Torr, pounds per square inch, or other appropriate unit.

According to various embodiments, and with additional reference to FIG. 2, a catheter 10' is illustrated that may be substantially similar or identical to the catheter 10. The catheter 10' may also include a distal terminal end 12' and a proximal terminal end 16' and one or more ports 20' through an external wall 15' of the catheter 10 to an internal lumen 17' of the catheter 10'. A maximum external cross-sectional dimension may also be defined generally within a length 22'. The catheter 10' may also include one or more pressure sensors 30'-30'*b*, as illustrated in FIG. 2. The position of the various pressure sensors 30'-30'*b*, however, may be at different locations along the length 22' including the ports 20'.

As illustrated in FIG. 2, the first pressure sensor 30' may be positioned at a proximal extent of the ports 20' and the third pressure sensor 30'*b* may be positioned substantially across from or adjacent to the first pressure sensor 30'. The second pressure sensor 30'*a* may be positioned at or substantially adjacent to distal terminal end 12'. The plurality of pressure sensors 30'-30'*b* allow for measuring of pressure at both the distal end of the catheter 10' and at a point substantially adjacent or immediately at the proximal extent of the ports 20' generally defined by the distance 22'. Accordingly, the catheter 10', which may have a structure substantially similar or identical to the catheter 10, may be able to provide measurements of pressure at different locations relative to the length 22 that includes the ports 20' then the catheter 10 that includes the length 22 and the ports 20. Nevertheless, it is also understood that the pressure sensors may be provided in any appropriate number and appropriate location relative to the catheter 10 for measuring the pressure relative to a selected portion of the catheter 10, such as within the ventricle as discussed further herein.

The pressure sensors 30*a*-30*b* and/or 30'-30'*b* may be formed on the surface of the catheter 10, 10' according to various known techniques. For example, a thin wire may be placed on the selected surface of the catheter 10, 10' to form the sensor. Also, the sensor 30 may be formed as a thin film and applied to the surface, as noted above. Exemplary sensors may include those disclosed in Kim et al., Materials For Multifunctional Balloon Catheters With Capabilities And Cardiac Electrophysiological Mapping And Oblation Therapy, Nature Materials, pages 1-8 (6 Mar. 2011), incorporated herein by reference. The surface on which the sensor is formed, however, may be an exterior sensor or an internal surface upon which the sensor may be formed. For example, the sensor 30-30*b* or 30'-30'*b* may be formed on an internal surface that forms the lumen 17, 17'.

Figure 3A:
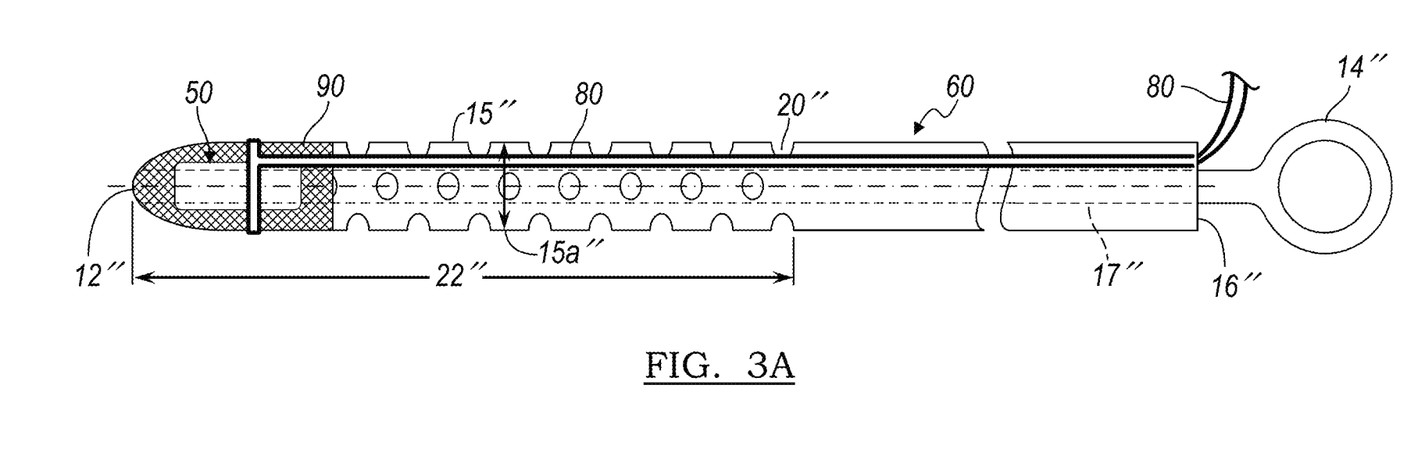
FIG. 3A is a schematic illustration of a shunt, including a sensor chip, according to various embodiments.
Figure 3B:
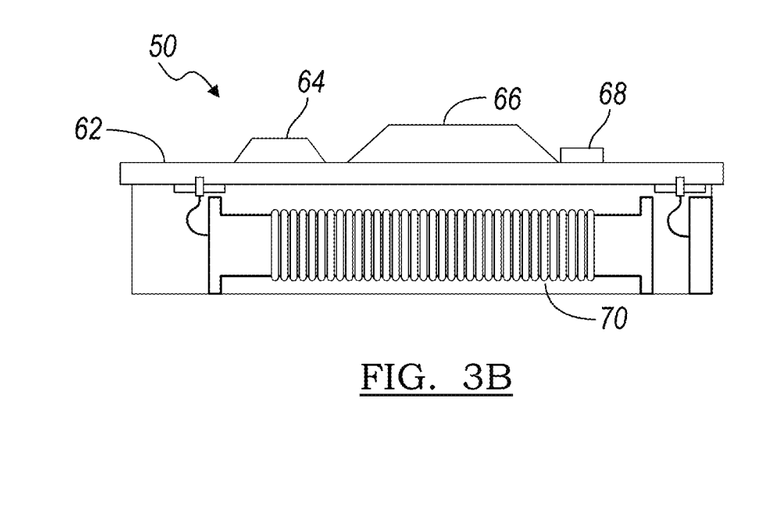
FIG. 3B is a first plain view of the sensor illustrated in FIG. 3A.
Figure 3C:
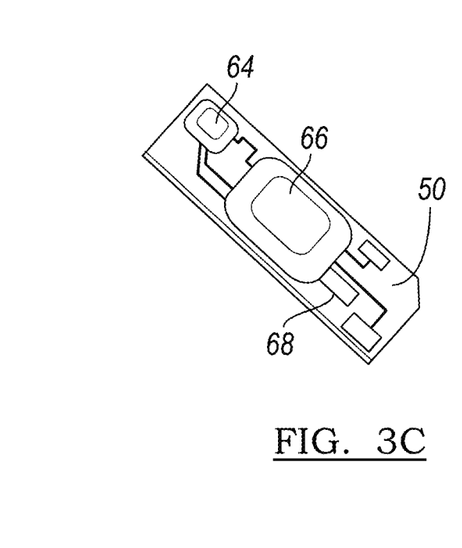
FIG. 3C is a top plain view of the sensor illustrated in FIG. 3A.

According to various embodiments, as illustrated in FIGS. 3A-3C, however, a sensor assembly 50 may be provided which may be attached on an exterior surface or internally to a catheter 60. The catheter 60 may be substantially similar to the catheters 10, 10' and may include portals 20" along a length 22" extending from a distal terminal end 12" towards a proximal terminal end 16". Further, the catheter 60 may include a lumen 17" to which the holes 20" allow fluid to flow. As discussed above, an external wall 15" of the catheter 60 may also have a maximum external cross-dimensional measurement 15" at least in the length 22. A stylet 14" may be placed in the lumen 17", such as to stiffen the catheter 60 for insertion in a subject and/or navigation, as discussed further herein. Nevertheless, the catheter 60 may be provided for insertion into a selected subject including the sensor assembly 50.

The sensor assembly 50 may be an appropriate sensor such as a micro or small pressure sensor sold by Phase IV Engineering, Inc. having a place of business located in Boulder, CO The sensor assembly 50 may include a circuit board 62 onto which various components are assembled including a capacitor 64, a processor system 66 (which may be encapsulated in an insulating material) and a sensor portion 68. The sensor portion 68 may be interconnected with the processor system 66 to assist in analyzing a pressure signal created by the pressure sensor 68.

The processor 66 may be any appropriate processor such as a general purpose processor executing instructions stored in a memory system and/or an application specific integrated circuit (ASIC) formed for the selected purpose of analyzing a signal from the pressure sensor 68. Accordingly, the pressure sensor assembly 50 may be provided in a substantially small package generally including dimensions of about 1 mm by about 5 mm, and further including dimensions of about 3 mm by about 10 mm. The circuit board 62 may provide a framework for communication between the various components, including the capacitor 64, the processor 66, and the pressure sensor 68. Further, interconnection may be provided to an antenna assembly 70.

The antenna assembly 70 can allow for transmission of a signal from the pressure sensor assembly 50 to a selected receiver or controller, discussed further herein. The pressure sensor assembly 50 may, therefore, include a power source such as a battery to provide power for the processor 66, other components, and the antenna 70. Alternatively, or in addition thereto, the pressure sensor assembly 50 may include a passive power system that may receive a signal from an exterior source to provide power to the pressure sensor assembly 50. According to various embodiments, the antenna assembly 70 may be at least a portion of an inductor circuit to allow for transmission of power to the pressure sensor assembly 50 from an external source via the antenna 70. Therefore, the antenna 70 may both transmit a pressure signal including information regarding a value of a measured pressure sensed by the pressure sensor 68 and receive a signal to provide power to the pressure sensor assembly 50.

Alternatively, or in addition thereto, a communication line or conductor 80 may also be provided to interconnect the pressure sensor assembly 50 with a selected transceiver or communicator. The conductor 80 may be similar to one or more of the conductors 32 discussed above to transmit the signal from the pressure sensor assembly 50 to a selected controller or receiver. The conductor 80, therefore, can transmit a signal regarding the pressure sensed by the pressure sensor 68 of the pressure sensor assembly 50 for analysis and further processing.

The pressure sensor assembly 50 may be interconnected with the catheter 60 in appropriate techniques. For example, a sleeve or coating member 90 may be placed over the pressure sensor assembly 50 to adhere or fix the pressure sensor assembly 50 to the catheter 60. The sleeve 90 may be formed of appropriate materials, such as Kevlar® polymer material, or other appropriate polymers. The sleeve 90 is generally provided to not interfere with the operability of the pressure sensor assembly 50 in determining a pressure near the catheter 60. Further, the line 80 may be provided to capture or hold the sleeve 90 in place.

As illustrated in FIG. 3A, the pressure sensor assembly 50 may be positioned substantially near or at the distal terminal end 12″. It is understood, however, as discussed above in relation to FIGS. 1A and 2 that the pressure sensor assembly 50 may be provided at any appropriate location along the length of the catheter 60. Further, more than one of the pressure sensor assemblies 50 may be provided along the length of the catheter 60 such as generally within the length 22″ of the catheter 60. Therefore, the pressure sensor assembly 50, or any selected number of the pressure sensor assemblies 50, may be provided to determine a pressure at selected positions along the length 22″ generally including the holes 20″.

According to various embodiments, as discussed above, determination of a pressure at a selected location or at a plurality of locations along the catheter 10, 10' or 60 can be determined. The determination of the pressures relative to the selected catheters 10, 10' or 60, can be used to determine a pressure within a selected ventricle, such as a lateral ventricle within a patient. It is also understood that various other pressures may be measured such as a pressure in a spinal column, pressure near a heart, or other appropriate location. As discussed further herein, however, determining a pressure within a ventricle, such as a ventricle within a cranial cavity within a brain, can be used to determine efficacy of a shunt implanted into a subject for drainage or removal of CSF from the ventricle within the cranial cavity. Accordingly, the pressure sensors, including those discussed above according to various embodiments, can be used to determine efficacy and achieving a selected result of a shunt system to alleviate hydrocephalous.

In addition to the various embodiments discussed above, it is understood that various systems can be provided that may be integrated with the catheters, including the catheter 10, 10', 60. Various sensors can include those disclosed by Kim et al., Materials For Multifunctional Balloon Catheters With Capabilities And Cardiac Electrophysiological Mapping And Oblation Therapy, Nature Materials, pages 1-8 (6 Mar. 2011), incorporated herein by reference. Additionally, pressure sensors can include those sold by MC10 Inc., having a place of business in Cambridge, Massachusetts. The sensors sold by MC10 may be integrated directly into or onto thin elastic membranes of conventional instruments, such as balloon catheters or flexible shafts. Additionally, sensors, such as the sensor assembly 50, may include micro, miniature, or ultra-miniature passive wireless sensors sold by Phase IV Engineering, Inc., having a place of business in Boulder, Colorado Other sensors may be adapted from Positive ID Corporation including the Glucochip™ assembly that includes an integrated antenna.

Further, in addition to the specific sensors as exemplarily discussed above, various coils may be provided to allow for induction to power the various sensors. For example, Metrigraphics, having a place of business in Wilmington, Massachusetts, sells flexible micro-circuits including the single layer and multi-layer flexible circuits that may be provided in an appropriate antenna size to allow for induction. Tech-Etch, Inc. having a place of business in Plymouth, Massachusetts, also as provides flexible circuits that may be used as antennas. Accordingly, the coils, such as the flexible circuit coils may be used to power the sensors as discussed further herein.

Generally, it is selected to have a pressure sensor that is small. Thus, the small sensor may be integrated into the catheter and the catheter may have a dimension no greater than the dimension of the generally provided catheter, including the Ares® catheter sold by Medtronic Neurological. That is, the sensor is generally selected to be provided on the catheter, such as the catheter 10 and/or the catheter 60 without increasing or substantially increasing the external dimensions of the catheter as generally sold without a sensor. Accordingly, it may be selected to have the sensor be provided on the catheter without increasing the dimensions of the catheter more than about 10% or more than about 20% or 0% relative to a catheter not having any pressure sensors. This may include increasing the dimensions of the catheter no more than 20%. The dimension that is selected to be maintained is the cross-sectional maximum dimension, such as at least within the length 22, 22', 22″. Further, it is generally selected to have the sensor have as close to zero or zero drift over time. That is, that the pressure sensor may be calibrated prior to placement or implantation and the calibration would vary or the measurement would vary less than about 1% to about 10%, including about 5% over a selected lifespan of the pressure sensor. As a further example, it may be desirable to have less than a 1% drift in a pressure measurement over five year lifespan of an implanted catheter.

Figure 4:
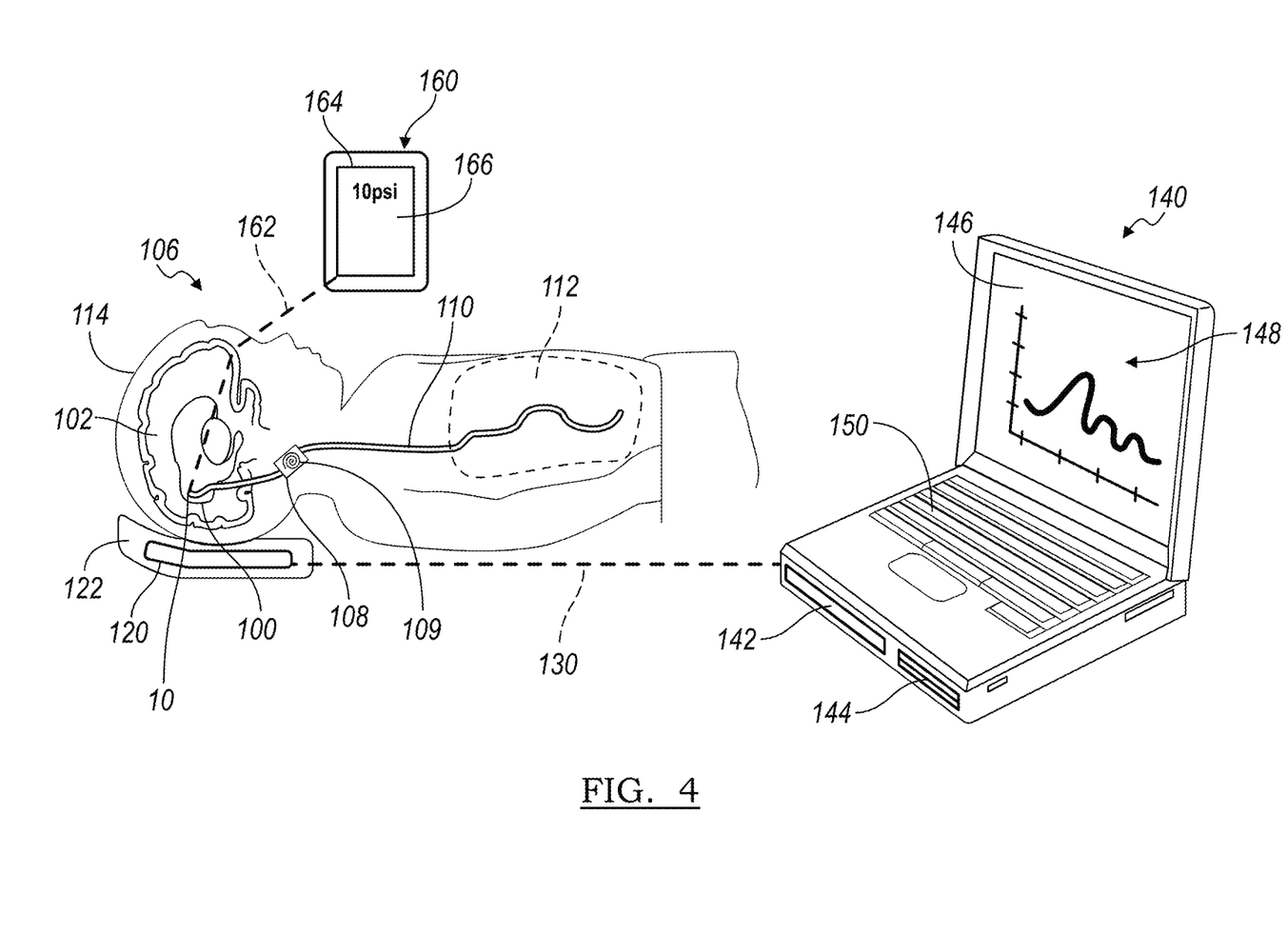
FIG. 4 is a schematic view of a pressure monitoring system.

The various pressure sensors provided on the catheters, including the catheters 10, 10', and 60 may be used for various purposes, such as measuring pressure within a ventricle. As discussed above, the catheter may be positioned within a ventricle of a patient as schematically illustrated in FIG. 4. As exemplarily illustrated in FIG. 4, the catheter 10 may be positioned within a lateral ventricle 100 of a brain 102 of a subject 106. The subject 106 may be any appropriate subject, such as a human subject, including a human child or adolescent. In certain instances, the CSF may not drain from the ventricles, including the lateral ventricle 100 within the brain 102 of the subject 106, causing hydrocephalous. In these instances, a shunt and/or catheter system, which may include the catheter 10, may be implanted within the lateral ventricle 100 to provide a pathway for CSF to flow from the lateral ventricle 100 out of the brain 102.

In various procedure examples, the catheter 10 may be interconnected or connected to a valve 108, which may be the Strata® valve sold by Medtronic Neurosurgery. It may be selected, however, but the valve may not be included for various purposes. Further, the valve 108 may have an inductive antenna 109 associated therewith, such as placed on a surface of the valve 108. Generally, the valve 108 may be placed near a skin surface of the subject 106, thus inductive coupling may be more efficient. The conductive traces, such as the traces 32-32*b* may then transfer the power to the sensors 30-30*b*. Accordingly, inductive power antennas need not be placed directly with the sensors 3.0-30*b*, or other appropriate pressure sensors.

The catheter 10 may further be interconnected with a drainage cannula 110 that may be positioned in an appropriate portion of the subject 106, such as near the abdomen in the peritoneal cavity 112, as discussed above. Also it is understood that the cannula 110 may be interconnected with an external collection system or package rather than draining internally into the subject 106. As is generally understood in the art, hydrocephaly causes pressure on the brain 102 due to the buildup of fluid within the ventricles, including the lateral ventricle 100, and presses the brain 102 against a skull 114 of the subject 106. Accordingly, providing passage for the CSF from the lateral ventricle 100 out of the brain 102 can reduce or eliminate the effects of hydrocephaly.

If the catheter 100, or portions of the drainage system become clogged or the increase of CSF is greater than originally designed parameters, pressure may increase within the lateral ventricle 100 above a selected, such as a predetermined, value. Such a malfunctioning or failed shunt will allow pressure to again build and possibly cause damage to the brain of the subject 106. This damage may occur before signs or symptoms clinically present again in the subject 106. This damage may be temporary, long term, or permanent. To minimize this damage, real time pressure monitoring of cerebral spinal fluid in cerebral ventricles may allow for early detection and treatment prior to damage. Therefore, the pressure sensors, including those discussed above, may be provided on the catheter 10, or any of the appropriate catheters discussed above according to various embodiments, to monitor the pressure within the lateral ventricle 100 or in other appropriate positions where the catheter 10 is implanted. It is understood that discussion of the catheter 10 herein, as an example, is not intended to disregarded the other disclosed catheters unless specifically so stated. Similarly, discussion of the pressure sensor 30 is not intended to limit the disclosure to only that pressure sensor and not the other pressure sensors including disclosed embodiments, unless specifically stated.

Generally, as discussed above, the catheter 10 may include a pressure sensor positioned thereon. The pressure sensor, such as the pressure sensor 30, may measure a pressure at the sensor 30 and the pressure may be recorded over time as a pressure value. Further, as discussed above, the communication with the pressure sensor 30 may be wireless. Alternatively, or in addition thereto, the communication may be wired. Regardless, a receiver and/or transmitter (transceiver) 120 can be provided to be positioned near the catheter 10 in the implanted position, such as within or under a pillow 122 and/or within or under a bed or patient support. The subject 106 may lie on the pillow 122 and the transceiver 120 may receive the pressure signals from the pressure sensor 30 positioned in the lateral ventricle 100.

If the pressure sensor 30 is wireless, the transceiver 120 may transmit a signal to power the induction antenna, as discussed above, and/or may transmit a signal to indicate that the pressure sensors transmit a signal if an internal battery is provided. Alternatively, the transceiver 120 may be physically connected, such as with the leads or conductors 32 to transmit the pressure signal to the transceiver 120. The transceiver 120 may be an appropriate transceiver such as the transceiver CareLink® Reader sold by Medtronic, Inc. Generally, the transceiver 120 may receive a pressure signal from the pressure sensor 30 and transmit it via a communication line 130 to a workstation 140.

The workstation 140 may receive the pressure signal from the transceiver 120 that is received from the pressure sensor 30. The communication line 130 may be a wired data transmission line and/or a wireless transmission (e.g., Bluetooth® communication protocol). The workstation 140 may allow the user to select the times and frequency of monitoring by the pressure sensor 30. Thus, the pressure sensor need not constantly measure the pressure. This may be a power saving routine. Also, if the pressure sensor 30 is passively powered, it may only measure when a user instructions the transceiver 120 to emit the power signal. Thus, measuring of the pressure may be continuous or at any selected frequency.

The workstation 140 may be an appropriate workstation, such as a portable computer (such as a portable or handheld workstation 160), terminal for a networked processor, or any other appropriate workstation. Nevertheless, the workstation 140 may include a processor 142 and a memory system 144. The processor 142 may be an application specific processor, such as an application specific integrated circuit. Alternatively, or in addition thereto, the processor 142 may be a general processor that is configured to execute instructions, as discussed further herein. Instructions may be stored on the memory 144 which may be any appropriate type of memory such as a read/write memory, random access memory, local memory, or remotely connected memory. Further, sensor information or data from the sensor 30 may be stored on the memory 144 for later retrieval and/or processing. The workstation 140 may further include a display 146 to display information, such as a graph 148 of the pressure measurements over time. Further, the workstation 140 may include a user input such as a touchscreen display, a pointer device, or other appropriate inputs.

The transceiver 120 used with the workstation 140 can provide an external measuring and/or analysis system which may be generally referred to as a pressure analysis system. Further, it is understood that the transceiver 120 may be integrated into the workstation 140 and the workstation 140 with the integrated transceiver 120 may be positioned close enough to the catheter 10 to receive a transmission of a pressure signal from the pressure sensor 30 on the catheter 10. In this way, the workstation 140 may provide a compact and efficient system for receiving the pressure signals from the pressure sensor 30 to provide for analysis thereof.

In various embodiments, the workstation 140 may include a handheld portable device such as an iPhone® communication system, or similar device. A user, such as a nurse, doctor, or the like, may position the handheld device exemplarily illustrated as 160 in FIG. 4, near the subject 106 to receive a pressure signal from the pressure sensor 30 on the catheter 10. The pressure signal may be transmitted wirelessly, which is schematically illustrated as transmission 162, such as via a Bluetooth® wireless transmission protocol. The transmitted signal may be analyzed by an onboard processor or a remote processor for viewing an instantaneous and/or graphed pressure value 164 on a display 166 of the handheld device 160.

According to various embodiments, therefore, the workstation 140, which may be embodied as a handheld device 160, may be used to view a pressure value sensed by the pressure sensor 30 on a catheter 10. This can allow a user to monitor pressure in the lateral ventricle 100, or other appropriate location, to ensure that the appropriate pressure, such as a predetermined pressure, is being maintained within the brain 102 of the subject 106. The predetermined pressure may be a single value, a range of values, or a single value with a threshold range (e.g. plus or minus the selected predetermined value).

As discussed above, hydrocephaly may increase pressure in the brain 102 within the skull 114. Such increased pressure may manifest itself as headaches or other trauma to the patient. Prior to trauma occurring to the patient, however, a pressure may generally increase within the skull 114, such as within the lateral ventricle 100 to a level that is pretraumatic but higher than a predetermined or preselected value. Accordingly, a monitoring, such as constant or at a selected frequency or time, such as with a workstation 140, can allow for a determination that the pressure is increasing to an undesirable or unselected level and intervention may occur prior to trauma occurring to the subject 106. Therefore, any monitoring with the workstation 140, and also the handheld workstation 160, may lead to an output to a user, such as an alarm being sounded or provided to a selected individual, such as a nurse or doctor. For example, a text message, audible alarm, color alarm, or other alarm may be provided to indicate that the pressure measured by the pressure sensor 30 on the catheter 10 is above or outside of a selected range.

Figure 5A:
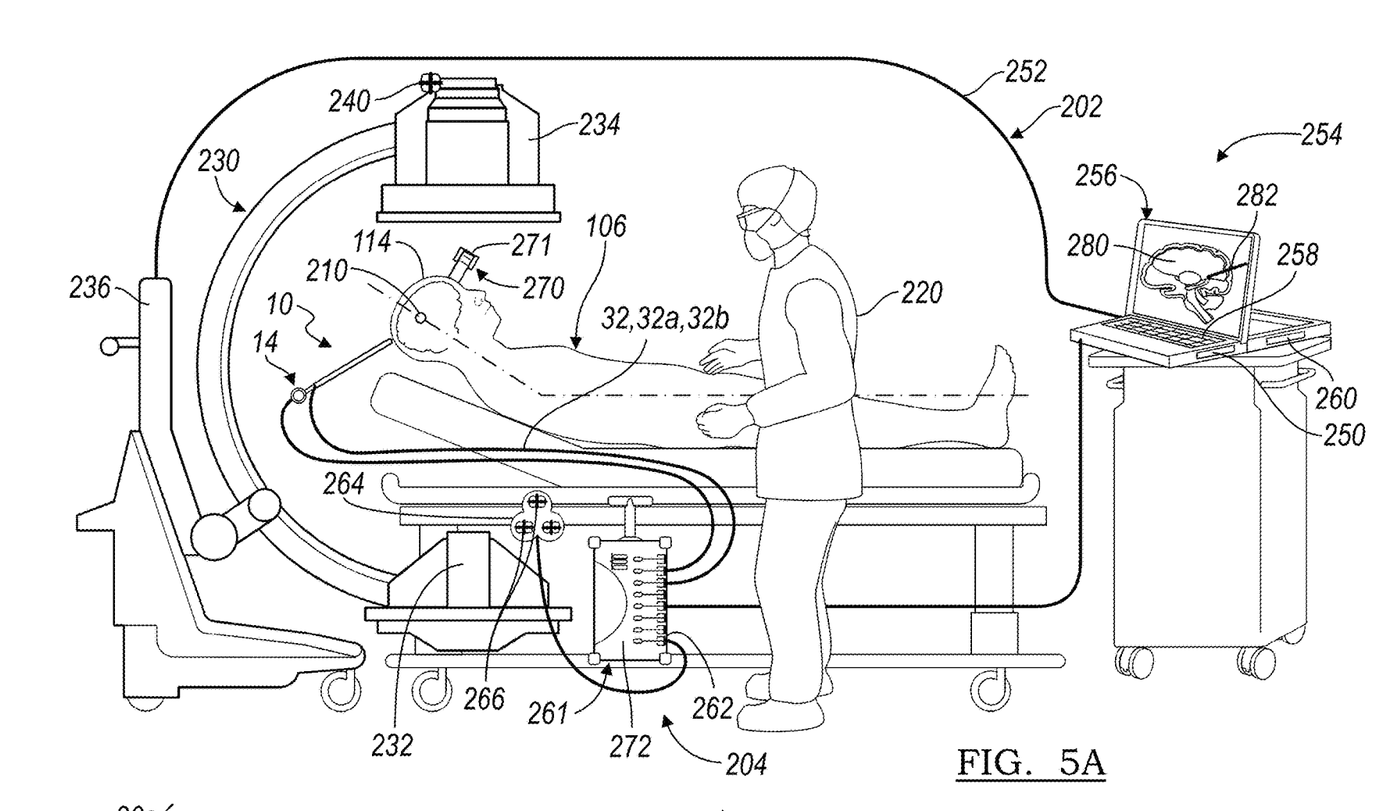
FIG. 5A is a view of a navigation and imaging system.
Figure 5B:
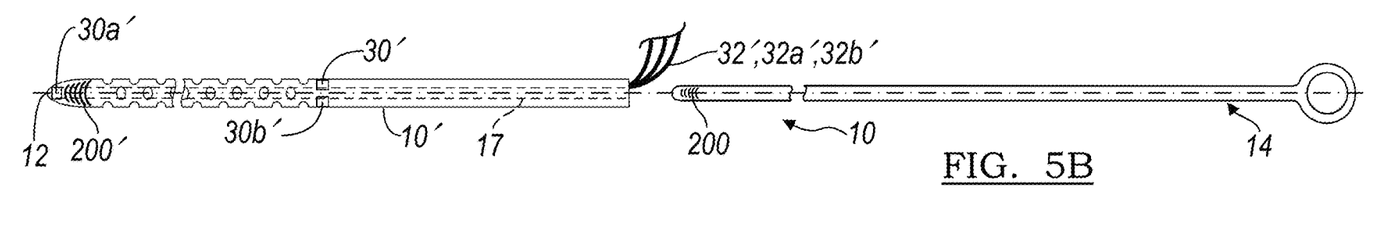
FIG. 5B is an unassembled view of a stylet and a catheter.

Turning reference to FIGS. 5A and 5B, the catheter, including catheter or stent 10, 10' discussed above, may be positioned within the subject 106 with a navigated instrument. The navigated instrument may include a tracking device or element 200' positioned directly on the catheter 10, or a catheter according to any various embodiment, or may be included with the stylet 14. Tracking devices may include electromagnetic tracking devices including coils of wire, conductive materials, or the like, formed on the catheter 10 or on the stylet 14. According to various embodiments, the stylet 14 may include a tracking device 200 formed near a distal end of the stylet 14. The stylet 14 may be placed within the lumen 17 of the catheter as illustrated in FIG. 1, and further in FIG. 5B.

The tracking device 200 may be interconnected with a navigation system 202, as illustrated in FIG. 5A. The navigation system, as discussed further herein, may include a tracking system 204 that can track the tracking device 200 in space including a three-dimensional X,Y,Z position and three-dimensional pitch, yaw, and roll orientation to determine a position and orientation of the tracking device 200 in space. The stylet 14 can be rotationally and axially fixed within the catheter 10 to allow for a determination of a portion or all of the catheter 10, including the portion adjacent to the tracking device 200. Alternatively, the catheter 10 may include the tracking device 200' that allows for directly tracking the catheter 10 during an implantation and positioning of catheter 10. Appropriate tracking devices can include tracking devices as disclosed in U.S. Pat. No. 8,644,907, incorporated herein by reference. Additionally, the navigation system can include the navigation system disclosed in U.S. Patent Application Publication 2014/0323852, incorporated herein by reference.

With continuing reference to FIGS. 5A and 5B, the catheter 10 may be inserted into the patient 106 via an opening or bore 210 in the skull 114 of the subject 106. The bore 210 may be a burr hole formed through the skull 114 as generally understood in the art. The catheter 10, tracked either directly via the tracking device 200' or via the tracking device 200 on the stylet 14, can then be inserted into the hole 210. The navigation of the catheter 10 relative to the subject 106 may proceed according to various navigation procedures and techniques, such as those generally known in the art and discussed below, to ensure or assist in positioning the catheter 10 in a selected, including a predetermined or preselected location, within the subject 106. Further, although the following description is related generally to positioning the catheter 10 within a lateral ventricle of the brain 102, it is understood that catheter 10 may be positioned to any appropriate location to assist in movement or transport of liquid from one location to another.

The navigation system 202, which may include an electromagnetic navigation system, is primarily described with respect to performing a procedure on a human patient, the navigation system 202 may be used to perform a procedure on other animate and/or inanimate subjects, including those navigation systems as disclosed in U.S. Pat. App. Pub. No. 2014/0323852, incorporated herein by reference. Also, procedures disclosed herein can be performed relative to a volume, a mechanical device, and/or an enclosed structure. The volume may be of an animate or inanimate object. The subject can be an object that includes an enclosed mechanical device.

The navigation system 202 assists in performing a navigated or guided procedure. The guided procedure can be, for example, a surgical procedure, a neural procedure, a spinal procedure, and an orthopedic procedure. The navigation system 202 allows a user, such as a surgeon 220, to view on a display 22 a position of an instrument, such as the catheter 10, or other appropriate instrument that may be tracked in a coordinate system. The coordinate system can be related to an image, such as in an image guided procedure, or can be related to an imageless procedure.

The navigation system 202 can operate as an image-based system or as an imageless system. While operating as an imageless system, the navigation system 202 can register a subject space (generally defined within and near the subject 106) to a graphical display representing an area of the subject 106, rather than to both the subject space and an image space. Image data of the subject 106 need not be acquired at any time, although image data can be acquired to confirm various locations of instruments or anatomical portions of the subject 106. Positions of the subject 106 can be tracked and positions of the instrument 10 relative to the subject 106 can be tracked.

While operating as an imageless system, a position of an anatomical structure can be determined relative to the instrument and the positions of the anatomical structure and the instrument can be tracked. For example, a plane of an acetabulum can be determined by touching several points with the instrument 110. As another example, a position of a femur can be determined in a similar manner. The position of the instrument 10 and the anatomical structure can be shown on a display with icons or graphics. The display, however, may not show actual image data captured of the subject 106. Other data can be provided, such as atlas data or morphed atlas data. The atlas data can be image data that is generated or generalized from the subject 106. For example, a brain atlas can be generated based on detail analysis of image data of a brain of a patient. Operation of the navigation system 202 as an image based system is further described below.

Although the navigation system 202 is described as acquiring image data using an imaging device 230, other data may be acquired and/or used, such as patient and non-patient specific data. The imaging device 230 acquires pre-, intra-, or post-operative image data and/or real-time image data of a subject 106. The imaging device 230 can be, for example, a fluoroscopic x-ray imaging device that may be configured as a C-arm having an x-ray source 232 and an x-ray receiving device 234. Other imaging devices may be included and mounted on the imaging device 230. Calibration and tracking targets and radiation sensors may be included.

The navigation system 202 may further include an imaging device controller 236. The imaging device controller 236 controls the imaging device 230 to (i) capture x-ray images received at the x-ray receiving section 234, and (ii) store the x-ray images. The imaging device controller 236 may be separate from the imaging device 230 and/or control the rotation of the imaging device 230. For example, the imaging device 28 can move in selected directions around the patient 106. Also, the imaging device may include an Oarm® imaging device as sold by Medtronic, Inc., having a place of business in Minnesota.

Further, an imager tracking device 240 may be included to track a position of selected portions of the imaging device 230 to identify the position of the imaging device 230 relative to the subject 106 while acquiring the image data to assist in registration. The image data can then be forwarded from the imaging device controller 236 to a processing module of a navigation computer 254 wirelessly or via a link 252. The navigation computer 254 can include a processing module that is configured to execute instructions to perform a procedure.

A work station 254 can include the navigation computer 254, a navigation display 256, a user interface 258, and an accessible memory system 260. The image data may be transmitted from the controller 236 to the work station 254 or to a tracking system 204. The workstation 254 may be a portable computer, such as a laptop computer or a tablet computer. The navigation computer 254 including the computer module may include a general purpose processor that executes instructions for navigating the catheter 10 and/or may include an application specific circuit.

The tracking system 204, as discussed further herein, may include a coil array controller (CAC) 261 having a navigation device interface (NDI) 262.

While the imaging device 230 is shown in FIG. 5A, any other alternative 2D, 3D or 3D imaging acquired over time to include four dimensions, imaging modality may also be used. For example, any imaging device, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative, computed tomography (CT), single photo emission computed tomography (SPECT), and/or planar gamma scintigraphy (PGS) imaging devices may be used. Any of these imaging devices may be used to acquire pre- or post-operative and/or real-time images or image data of the subject 106. The images may also be obtained and displayed, generally, in two or three dimensions. In more advanced forms, 3D surface rendering regions are achieved of the subject, which may be rendered or changed in time (fourth dimension). The 3D surface rendering regions may be achieved by incorporating subject data or other data from an atlas or anatomical model map or from pre-operative image data captured by MRI, CT, or echocardiography modalities. Image data sets from hybrid modalities, such as positron emission tomography (PET) combined with CT, or single photon emission computer tomography (SPECT) combined with CT, can also provide functional image data superimposed onto anatomical data to be used to reach target sites within the subject 106.

The navigation system 202 further includes the tracking system 204. The tracking system 204 includes a localizer 264, which may also be referred to as a transmit coil array (TCA), a tracking array, or a transmit coil assembly. The TCA 264 includes coil arrays 266 that can transmit or receive. The tracking system 204 includes the CAC 261. The localizer 264, the instrument tracking device 200 of the stylet 14 or the tracking device 200' of the catheter 10. It is understood that the tracked portion may be generally referred to as an instrument and that the tracking device may be generally referred to as an instrument tracking device. The tracking system may also track a dynamic reference frame (DRF) 270. All tracked portions are connected to the CAC 261 via the NDI 262. The CAC 260 and the NDI 262 can be provided in a CAC/NDI container 272. The NDI 262 may have communication ports that communicate with the localizer 264, the instrument tracking device 200 and/or the DRF 270 wirelessly or via wires.

The coil array localizer 264 can transmit signals that are received by the DRF 270 and at least one tracking device (e.g., the instrument tracking device 200). The tracking device 200 can be associated with the instrument 14 at a location that is generally positioned within the subject 106 during a procedure. The DRF 270 can then transmit and/or provide signals, from a DRF tracking device 271, based upon the received/sensed signals of the generated fields from the localizer 270 and/or other localizers. It is understood that the tracking system may also be operated in reverse, where the tracking devices 200, 270 transmit a field that is sensed by the TCA 264.

The DRF 270 can be connected to the NDI 262 to forward the information to the CAC 261 and/or the navigation computer 250. The DRF 270 may be fixed to the subject 106 and adjacent to the region where navigation is occurring such that any movement of the subject 106 is detected as relative motion between the localizer 264 and the DRF 270. The DRF 270 can be interconnected with the subject 106. Any relative motion is indicated to the CAC 260, which updates registration correlation and maintains accurate navigation.

In operation, the navigation system 202 creates a map between points in image data or an image space, such as one defined by an image 280 shown on the display 256, and corresponding points in a subject space (e.g., points in an anatomy of a patient or in a patient space). After the map is created, the image space and subject space are registered to each other. This includes correlating position (location and orientations) in an image space with corresponding positions in a subject space (or real space). Based on the registration, the navigation system 202 may illustrate an icon 282 (which may include a three-dimensional rendering of the instrument, including the catheter 10 and/or the stylet 14) at a navigated position of the instrument 14 relative to an image of the subject 106 in a super-imposed image. For example, the icon 282 can be illustrated relative to a proposed trajectory and/or a determined anatomical target. The work station 254 alone and/or in combination with the CAC 261 and/or the C-arm controller (or control module) 236 can identify the corresponding point on the pre-acquired image or atlas model relative to the tracked instrument 14; and display the position on display 256 and relative to the image 280. This identification is known as navigation or localization. The work station 254, the CAC 261, and the C-arm controller 236 and/or selected portions thereof can be incorporated into a single system or implemented as a single processor or control module.

To register the subject 106 to the image 280, the user 220 may use point registration by selecting and storing particular points from the pre-acquired images and then touching the corresponding points on the subject 106 with a pointer probe or any appropriate tracked device. The navigation system 202 analyzes the relationship between the two sets of points that are selected and computes a match, which allows for a correlation of every point in the image data or image space with its corresponding point on the subject 106 or the subject space.

The points that are selected to perform registration or form a map are the fiducial markers, such as anatomical or artificial landmarks. Again, the fiducial markers are identifiable on the images and identifiable and accessible on the subject 106. The fiducial markers can be artificial landmarks that are positioned on the subject 106 or anatomical landmarks that can be easily identified in the image data.

The navigation system 202 may also perform registration using anatomic surface information or path information (referred to as auto-registration). The navigation system 202 may also perform 2D to 3D registration by utilizing the acquired 2D images to register 3D volume images by use of contour algorithms, point algorithms or density comparison algorithms.

In order to maintain registration accuracy, the navigation system 202 tracks the position of the subject 106 during registration and navigation with the DRF 270. This is because the subject 106, DRF 270, and localizer 264 may all move during the procedure. Alternatively the subject 106 may be held immobile once the registration has occurred, such as with a head holder. Therefore, if the navigation system 202 does not track the position of the subject 106 or an area of an anatomy of the subject 106, any subject movement after registration would result in inaccurate navigation within the corresponding image. The DRF 58 allows the tracking system 204 to track the anatomy and can be used during registration. Because the DRF 270 is rigidly fixed to the subject 106, any movement of the anatomy or the localizer 264 is detected as the relative motion between the localizer 264 and the DRF 270. This relative motion is communicated to the CAC 261 and/or the processor 250, via the NDI 262, which updates the registration correlation to thereby maintain accurate navigation.

The tracking system 204 can position the localizer 264 adjacent to the patient space to generate an EM field (referred to as a navigation field). Because points in the navigation field or patient space is associated with a unique field strength and direction, the tracking system 204 can determine the position (which can include location and orientation) of the instrument 14 by measuring the field strength and direction or components of the EM field at the tracking device 200. The DRF 270 is fixed to the subject 106 to identify the location of the subject 106 in the navigation field. The tracking system 204 continuously determines the relative position of the DRF 270 and the instrument 14 during localization and relates this spatial information to subject registration data. This enables image guidance of the instrument 14 within and/or relative to the subject 106.

To obtain a maximum accuracy it can be selected to fix the DRF 270 in each of at least six degrees of freedom. Thus, the DRF 270 or any tracking device, such as the tracking device 200, can be fixed relative to axial motion X, translational motion Y, rotational motion Z, yaw, pitch, and roll relative to a portion of the subject 106 to which the DRF 270 is attached. Any appropriate coordinate system can be used to describe the various degrees of freedom. Fixing the DRF 270 relative to the subject 106 in this manner can assist in maintaining maximum accuracy of the navigation system 202.

The instrument 14 can include the stylet, as discussed above. However, the included discussion may also include the catheter 10, 10', 60 as the instrument. Thus, reference to the instrument 14 is not intended to limit the instrument that may be tracked and navigated.

Accordingly, the navigation system 202 can be used to place the catheter 10 with the tracking system 204. As discussed above, this can be performed by acquiring image data of the subject 106, including MRI image data. The MRI image data may be analyzed to determine the location for positioning of the catheter 10, such as in a selected ventricle, including lateral ventricle, first, second, or third ventricles, etc. This position can be identified as an anatomical target to assist in navigation. The navigation system 202 may then register the subject space of the subject 106 to the image space of the image 280 and the location of the catheter 10 can be identified as a superimposed icon 282 on the image 280. The user 220 can then view the display 256 while moving the catheter 10 into the skull 114 and the brain 102 of the subject 106 to position the catheter 10. The user 220 need not, therefore, directly view the catheter 10 to determine its position within the subject 106. As discussed above, the catheter 10 may include the tracking device 200' directly thereon or the position of the catheter 10 may be determined based upon the tracking of the tracking device 200 on the stylet 14 positioned within the catheter 10. Tracking a stylet, such as the stylet 14, positioned within a lumen or cannula of an instrument may occur according to various embodiments, including those disclosed in U.S. Pat. No. 8,644,907, incorporated herein by reference.

Nevertheless, the user 220, or any appropriate user, can determine positioning of the catheter 10 within the subject 106 for implanting a shunt system to treat the subject 106, such as treating hydrocephaly. The positioning of the catheter 10 within the subject 106 can be performed with the navigation system 202 to assist in ensuring or confirming that a selected location of the catheter 10 is reached during or following implantation. Once implantation of the catheter 10 has occurred, the pressure within the lateral ventricle 100 can then be monitored using the pressure sensors, such as the pressure sensor 30, discussed above. The monitoring system 140, including the transceiver 120, can then be used to constantly monitor, or at selected times or frequency monitor, the pressure at the catheter 10, including within the lateral ventricle 100. Therefore, the catheter 10 can be positioned at a substantially precise location within the brain 102 of the subject 106 with the navigation system 202 and the pressure within the lateral ventricle 100 can be consistently monitored with the pressure sensor, such as the pressure sensors 30 included with the catheter 10.

Further, it is understood, that the catheter 10 need not be implanted with the navigation system 202 and can be implanted with any appropriate system according to any appropriate procedure. Further, it is understood that although the exemplary embodiments discussed above refers to catheter 10, that any appropriate catheter or shunt may be implanted and include appropriate pressure sensors, such as those discussed above. Accordingly, the catheter 10 is generally directed towards the catheter to be implanted, but may also refer to the catheter 10' and the catheter 60. Moreover, any appropriate pressure sensor, including those discussed above, may be provided with the respective catheters and the catheter 10 including only the pressure sensor 30, as discussed above, need not be provided. The pressure sensor discussed in the various exemplary embodiments may include any of the pressure sensors disclosed herein. Further, it is understood that a selected catheter may include a plurality of types of pressure sensors such as the pressure sensor 30 and the pressure sensor assembly 50.

With continuing reference to FIG. 5A, the pressure sensors 30-30$b$, 30'-30$b'$, according to various embodiments including those discussed above, may be used to provide pressure information to the navigation system 202. As disclosed above, the pressure information may be transmitted to the navigation system 202 wirelessly, wired, or in a combination thereof. The pressure information may be used with the navigation system, such as being presented on the display 256. The pressure information may assist the user 220 in providing relevant location information and for confirming a location. For example, a pressure measurement may be helpful in determining that the shunt is properly placed in a cerebral ventricle with a high pressure that is to be lowered. The pressure monitoring during navigation can help ensure that flow is occurring through the shunt from the selected implant location, that the shunt is placed away from the cerebrum, etc. Thus, the single from the pressure sensors may assist the user 220 in "feeling" the location of the instrument, including the shunt 10, within the subject 106.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for monitoring pressure in a subject, comprising:
   an elongated instrument configured to be placed within the subject, the elongated instrument having an elongated wall that extends a distance from a first terminal end to a second terminal end, the elongated instrument defining a lumen along at least a portion of the distance, the elongated instrument further defining a passage into the lumen;
   a plurality of portals formed through the elongated wall along a selected length configured to allow a fluid to flow into the lumen from an external environment; and
   a pressure sensor integrated with the elongated instrument and configured to measure a pressure within the external environment along the selected length, wherein the pressure sensor is configured to provide a pressure signal based on the measurement of the pressure at the external environment.

2. The system of claim 1, further comprising a monitoring system configured to receive the pressure signal and provide an output to a user based on the received pressure signal.

3. The system of claim 1, wherein the passage into the lumen extends through the first terminal end configured to drain the fluid flowing through the plurality of portals to a remote site.

4. The system of claim 2, wherein the pressure sensor wirelessly provides the pressure signal to the monitoring system.

5. The system of claim 1, wherein the pressure sensor further includes a plurality of pressure sensors extending along the selected length.

6. The system of claim 1, wherein the pressure sensor is a thin film pressure sensor formed on an external surface of the elongated wall.

7. The system of claim 6, wherein the thin film pressure sensor does not increase the maximum cross-sectional dimension of the elongated wall greater than about 20%.

8. The system of claim 1, wherein the pressure sensor is positioned a distance away from the second terminal end of the elongated instrument.

9. The system of claim 6, wherein the pressure sensor is configured to measure a pressure at the plurality of portals.

10. The system of claim 1, wherein the pressure sensor includes a plurality of pressure sensors, wherein a first pressure sensor is positioned at the second terminal end and a second pressure sensor is positioned proximal the plurality of portals, wherein the first pressure sensor and the second pressure sensor are positioned along the selected length.

11. The system of claim 1, wherein the pressure sensor includes a sensor portion and a processor system.

12. The system of claim 11, further comprising an antenna assembly configured relative to the processor system to allow for transmission of the pressure signal to a selected receiver.

13. The system of claim 12, wherein the antenna assembly is configured to receive a signal to provide power to the pressure sensor.

14. The system of claim 1, further comprising:
   a trace formed on a surface of the elongated instrument configured to connect the pressure sensor to a monitor;
   wherein the pressure sensor is formed as a composite of insulating, conductive, and elastic thin films on a surface of the elongated wall.

15. The system of claim 1, further comprising:
   a tracking device associated with the elongated instrument;
   a tracking system configured to track the tracking device;
   a navigation system configured to determine at least one of a position or orientation of the elongated instrument relative to the subject when placing the elongated instrument within the subject.

16. The system of claim 15, further comprising:
   a display device configured to display an image of the subject and an icon that represents an outline of the elongated instrument superimposed on the image of the subject;
   wherein the navigation system includes the tracking system; and
   wherein the navigation system is configured to superimpose the icon on the image of the subject based on the determined position of the elongated instrument relative to the subject.

17. The system of claim 1, further comprising an elongated stylet configured to be positioned within the lumen from the first terminal end.

18. The system of claim 17, wherein the stylet includes a tracking device used to track a position of the stylet and the elongated instrument.

19. The system of claim 1, further comprising a transceiver configured to be positioned near, but exterior to the subject, to receive the pressure signal from the pressure sensor.

* * * * *

UNITED STATES PATENT AND TRADEMARK OFFICE
CERTIFICATE OF CORRECTION

PATENT NO. : 11,844,597 B2
APPLICATION NO. : 17/845398
DATED : December 19, 2023
INVENTOR(S) : Brad Jacobsen It is certified that error appears in the above-identified patent and that said Letters Patent is hereby corrected as shown below:

In the Specification

Column 6, Detailed Description, Line 24, After "CO", insert --.--

Column 8, Detailed Description, Line 66, Delete "3.0-30b," and insert --30-30b,-- therefor Column 9, Detailed Description, Line 14, Delete "100," and insert --10,-- therefor Column 12, Detailed Description, Line 20, Delete "22" and insert --256-- therefor Column 12, Detailed Description, Line 35, Delete "10" and insert --110-- therefor Column 12, Detailed Description, Line 44, Delete "10" and insert --110-- therefor Column 13, Detailed Description, Line 6, Delete "28" and insert --230-- therefor Column 14, Detailed Description, Line 8, Delete "260" and insert --261-- therefor Column 14, Detailed Description, Line 21, Delete "270" and insert --264-- therefor Column 14, Detailed Description, Line 27, Delete "250." and insert --254.-- therefor Column 14, Detailed Description, Line 32, Delete "260," and insert --261,-- therefor Column 15, Detailed Description, Line 28, Delete "58" and insert --270-- therefor Signed and Sealed this
Twenty-ninth Day of October, 2024

Katherine Kelly Vidal
*Director of the United States Patent and Trademark Office*